US007129252B2

(12) United States Patent
Chen

(10) Patent No.: US 7,129,252 B2
(45) Date of Patent: Oct. 31, 2006

(54) SIX MEMBERED AMINO-AMIDE DERIVATIVES AN ANGIOGENISIS INHIBITORS

(76) Inventor: Guoqing P Chen, 515 Oakbury Ct., Thousand Oaks, CA (US) 91360

( * ) Notice: Subject to any disclaimer, the term of this patent is extended or adjusted under 35 U.S.C. 154(b) by 128 days.

(21) Appl. No.: 10/859,733

(22) Filed: Jun. 2, 2004

(65) Prior Publication Data

US 2004/0259916 A1 Dec. 23, 2004

Related U.S. Application Data

(60) Provisional application No. 60/478,937, filed on Jun. 16, 2003.

(51) Int. Cl.
*C07D 213/04* (2006.01)
*A61K 31/44* (2006.01)
(52) U.S. Cl. ...................... 514/332; 514/352; 514/357; 546/255; 546/308; 546/329

(58) Field of Classification Search ................ 514/332, 514/352, 357; 546/255, 308, 329
See application file for complete search history.

(56) References Cited

U.S. PATENT DOCUMENTS 5,712,279 A * 1/1998 Biller et al. ........... 514/253.01

* cited by examiner

*Primary Examiner*—Zinna N. Davis

(57) ABSTRACT

The present invention relates to six membered amino-amide derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

8 Claims, No Drawings

SIX MEMBERED AMINO-AMIDE DERIVATIVES AN ANGIOGENISIS INHIBITORS

This application claims the benefit of U.S. Provisional Application No. 60/478,937 filed on Jun. 16, 2003.

FIELD OF THE INVENTION

The present invention relates to six membered amino-amide derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

BACKGROUND OF THE INVENTION

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma. Tumor angiogenesis, the formation of new blood vessels and their permeability is primarily regulated by (tumor-derived) vascular endothelial growth factor (VEGF), which acts via at least two different receptors: VEGF-R1 (fms-like tyrosine kinase, Flt-1); and VEGF-R2 (kinase domain region, KDR/fetal liver kinase-1, Flk-1). The VEGF KDR receptor is highly specific for vascular endothelial cells (for review, see: Farrara et al. *Endocr. Rev.* 1992, 13, 18; Neufield et al. *FASEB J.* 1999, 13, 9).

VEGF, and more specifically VEGF-A, exists in the human species in three isoforms (through alternative splicing), which are named according to the number of amino acid residues: VEGF 121, VEGF 165 and VEGF 189. These isoforms have distinct functional properties in terms of heparin binding and diffusibility. A related factor, placenta growth factor (PlGF), only binds VEGF-R1/Flt-1.

VEGF expression is induced by hypoxia (Shweiki et al. *Nature* 1992, 359, 843), as well as by a variety of cytokines and growth factors, such as interleukin-1, interleukin-6, epidermal growth factor and transforming growth factor-α and β.

The membrane-bound VEGF receptors occur on the surface of activated endothelial cells and possess an intracellular tyrosine-kinase domain, which is necessary for intracellular signal transduction. It is thought that the VEGF dimer induces, upon binding, a dimerization of two receptor molecules, leading to autophosphorylation of the intracellular portion of the receptors and subsequent binding of SH2-containing proteins. Subsequent phosphorylation (activation) of phospholipase C, phosphatidylinositol-3 kinase and Ras GTPase-activating protein (GAP) has been demonstrated.

A large number of human tumors, especially gliomas and carcinomas, express high levels of VEGF and its receptors. This has led to the hypothesis that the VEGF released by tumor cells stimulates the growth of blood capillaries and the proliferation of tumor endothelium in a paracrine manner and through the improved blood supply, accelerate tumor growth. Increased VEGF expression could explain the occurrence of cerebral edema in patients with glioma. Direct evidence of the role of VEGF as a tumor angiogenesis factor in vivo is shown in studies in which VEGF expression or VEGF activity was inhibited. This was achieved with anti-VEGF antibodies, with dominant-negative VEGFR-2 mutants which inhibited signal transduction, and with anti-sense-VEGF RNA techniques. All approaches led to a reduction in the growth of glioma cell lines or other tumor cell lines in vivo as a result of inhibited tumor angiogenesis.

Three principal mechanisms play an important part in the activity of angiogenesis inhibitors against tumors: 1) Inhibition of the growth of vessels, especially capillaries, into vascular resting tumors, with the result that there is no net tumor growth owing to the balance that is achieved between cell death and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells which normally line the vessels.

The present invention is based on the discovery of compounds that surprisingly inhibit the effect of VEGF receptor tyrosine kinase, a property of value in the treatment of disease states associated with angiogenesis and/or increased vascular permeability such as cancer, diabetes, psoriasis, rheumatoid arthritis, Kaposi's, haemangioma, acute and chronic nephropathies, atheroma, arterial restenosis, autoimmune disease, acute inflammation, excessive scarformation and adhesions, lymphoedema, endometriosis, dysfunctional uterine bleeding and ocular diseases with retinal vessel proliferation as well as other angiogenesis and its related diseases.

Examples of anthranilic acid and nicotinic acid derivatives that are similar in structure to those of the present application are disclosed in the following patent applications: WO 02066470, WO 02068406, WO 0027819, WO 0027820, WO 0155114, WO 0185671, WO 0185691 and WO 0185715.

SUMMARY OF THE INVENTION

The present invention relates to novel six membered amino-amide derivatives of formula (I)

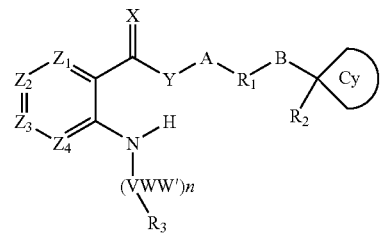

Formula (I)

Wherein
X is O or S;
Y is —N($R_4$)—;
$Z_1$, $Z_2$, $Z_3$ and $Z_4$ are independently $CR_5$ or N;
A is selected from direct bond, lower alkylenyl and lower alkenlenyl;
B is selected from direct bond, lower alkylenyl, lower alkenlenyl, —O—, —N($R_4$)—, —C(O)N($R_4$)—, —OC(O)N($R_4$)—, —N($R_4$)C(O)—, —N($R_4$)C(O)O—, —N($R_4$)C(O)N($R_4$)—, —C(O)—, —S(O)—, —S(O)$_2$—, —S(O)N $(R_4)$—, —$S(O)_2N(R_4)$—, —$N(R_4)S(O)$—, —$N(R_4)S(O)_2$—, —$N(R_4)S(O)N(R_4)$—, —$N(R_4)S(O)_2N(R_4)$—;

$R_1$ is selected from cycloalkyl, cycloalkenyl, aryl and heterocyclyl;

Cy is selected from cycloalkyl, cycloalkenyl and heterocyclyl;

$R_2$ is selected from halogen-lower alkyl, lower alkyl, lower alkenyl, lower alkynyl, $C_0$–$C_6$cyano, $C_0$–$C_6$hydroxy, $C_0$–$C_6$alkoxy, $C_0$–$C_6$alkoxyalkoxy, $C_0$–$C_6$amino, $C_0$–$C_6$alkoxyamino, $C_0$–$C_6$carboxy, $C_0$–$C_6$carboxyalkyl, $C_0$–$C_6$carbonylamino, $C_0$–$C_6$carbonylalkyl, $C_0$–$C_6$oxycarbonylalkyl, $C_0$–$C_6$oxycarbonylamino, $C_0$–$C_6$aminocarbonylalkyl, $C_0$–$C_6$aminocarbonyloxyalkyl, $C_0$–$C_6$aminocarbonylamino, $C_0$–$C_6$aminosulfonylalkyl, $C_0$–$C_6$cycloalkyl, $C_0$–$C_6$cycloalkenyl, $C_0$–$C_6$aryl, $C_0$–$C_6$oxyaryl, $C_0$–$C_6$alkoxyaryl, $C_0$–$C_6$aminoaryl, $C_0$–$C_6$aminoalkylaryl, $C_0$–$C_6$heterocyclyl, $C_0$–$C_6$oxyheterocyclyl, $C_0$–$C_6$alkoxyheterocyclyl, $C_0$–$C_6$aminoheterocyclyl and $C_0$–$C_6$aminoalkylheterocyclyl; wherein any above $C_1$–$C_6$ groups and amino groups can be optionally unsubstituted, mono-substituted or possibly disubstituted by lower alkyl;

$R_1$ and $R_2$ are combined together as a fused spiro ring G comprising C, N, O or S, wherein ring G is selected from cycloalkyl, cycloalkenyl, aryl and heterocyclyl, which can be saturated or partially saturated and unsubstituted, mono or polysubstituted;

V is C, N or $SO_2$;

W and W' are independently of each other hydrogen, halogen or lower alkyl; or together with the carbon atom to form a cycloalkyl, a cycloalkenyl, or a heterocyclyl ring;

n is an integer from 0 to 6;

$R_3$ is a heterocyclyl or an aryl;

$R_4$ is H or a lower alkyl;

$R_5$ is H, halogen or lower alkyl;

or of a N-oxide or a possible tautomer thereof;

or a pharmaceutically acceptable salt thereof

DETAILED DESCRIPTION OF THE INVENTION

The present invention is the directed to novel compounds which can inhibit VEGF receptor tyrosine kinase, and use of these compounds for inhibition of angiogenesis in the treatment of a neoplastic or proliferative or chronic inflammatory or angiogenic diseases which are caused by excessive or inappropriate angiogenesis in a mammal in need thereof.

In the compounds of formula (I),

X is O or S, preferably O;

Y is —$N(R_4)$—, preferably —NH—;

$Z_1$, $Z_2$, $Z_3$, $Z_4$ are independently CR$_5$ or N; preferably $Z_1$, $Z_2$, $Z_3$ are C and $Z_4$ is C or N as a phenyl or a pyridyl ring which is optional substituted up to three times independently by $R_5$;

A is selected from direct bond, lower alkylenyl and lower alkenlenyl; preferably direct bond or lower alkylenyl;

B is selected from direct bond, lower alkylenyl, lower alkenlenyl, —O—, —$N(R_4)$—, —$C(O)N(R_4)$—, —$OC(O)N(R_4)$—, —$N(R_4)C(O)$—, —$N(R_4)C(O)O$—, —$N(R_4)C(O)N(R_4)$—, —$C(O)$—, —$S(O)$—, —$S(O)_2$—, —$S(O)N(R_4)$—, —$S(O)_2N(R_4)$—, —$N(R_4)S(O)$—, —$N(R_4)S(O)_2$—, —$N(R_4)S(O)N(R_4)$—, —$N(R_4S(O)_2N(R_4)$—; preferably direct bond or lower alkylenyl;

$R_1$ is selected from cycloalkyl, cycloalkenyl, aryl and heterocyclyl; preferably phenyl which is optionally substituted by hydrogen, halogen or $R_2$;

Cy is selected from cycloalkyl, cycloalkenyl and heterocyclyl; preferably selected from cyclopropyl, cyclobutyl, cyclopentyl, cyclohexyl, 4 to 7 membered lactam and lactone;

$R_2$ is selected from halogen-lower alkyl, lower alkyl, lower alkenyl, lower alkynyl, $C_0$–$C_6$cyano, $C_0$–$C_6$hydroxy, $C_0$–$C_6$alkoxy, $C_0$–$C_6$alkoxyalkoxy, $C_0$–$C_6$amino, $C_0$–$C_6$alkoxyamino, $C_0$–$C_6$carboxy, $C_0$–$C_6$carboxyalkyl, $C_0$–$C_6$carbonylamino, $C_0$–$C_6$carbonylalkyl, $C_0$–$C_6$oxycarbonylalkyl, $C_0$–$C_6$oxycarbonylamino, $C_0$–$C_6$aminocarbonylalkyl, $C_0$–$C_6$aminocarbonyloxyalkyl, $C_0$–$C_6$aminocarbonylamino, $C_0$–$C_6$aminosulfonylalkyl, $C_0$–$C_6$cycloalkyl, $C_0$–$C_6$cycloalkenyl, $C_0$–$C_6$aryl, $C_0$–$C_6$oxyaryl, $C_0$–$C_6$alkoxyaryl, $C_0$–$C_6$aminoaryl, $C_0$–$C_6$aminoalkylaryl, $C_0$–$C_6$heterocyclyl, $C_0$–$C_6$oxyheterocyclyl, $C_0$–$C_6$alkoxyheterocyclyl, $C_0$–$C_6$aminoheterocyclyl and $C_0$–$C_6$aminoalkylheterocyclyl, wherein any above $C_1$–$C_6$ groups and amino groups can be optionally unsubstituted, mono-substituted or possibly disubstituted by lower alkyl; preferably $R_2$ is selected from cyano, methyleneoxomethyl, methylenehydroxy, methyleneamino, methylene N,N-dimethylamino, methyleneazetidine, methylenepyrrolidine, methylenepiperidine, methylenemorpholine, methylenepiperazine, N-methyl-methylenepiperazine, carbonyl-N,N-dimethylamino and carbonylN-methyl-piperazine;

$R_1$ and $R_2$ are combined together as a fused spiro ring G comprising C, N, O or S, wherein ring G is selected from cycloalkyl, cycloalkenyl, aryl and heterocyclyl, which can be saturated or partially saturated and unsubstituted, mono or polysubstituted; preferably G is selected from 5 to 7 membered saturated or partial saturated heterocyclyl ring which can be unsubstituted or mono or polysubstituted independently by halogen or $R_2$;

V is C, N or $SO_2$; preferably C;

W and W' are independently of each other hydrogen, halogen or lower alkyl; or together with the carbon atom to which they are attached as a cycloalkyl, a cycloalkenyl, or a heterocyclyl ring; preferably, W and W' are independently hydrogen or fluoro;

n is an integer from 0 to 6; preferably 0, 1, 2 or 3;

$R_3$ is a heterocyclyl or an aryl; preferably selected from pyridyl, pyrimidinyl, quinolinyl, quinazolinyl, indazole, indolinone and phenyl;

$R_4$ is H or a lower alkyl; preferably H;

$R_5$ is H, halogen or lower alkyl; preferably H or fluoro;

or of a N-oxide or a possible tautomer thereof;

or a pharmaceutically acceptable salt thereof

The term "lower alkylenyl", as used herein, unless otherwise indicated, includes 1 to 6 saturated —$CH_2$— radicals.

The term "lower alkenlenyl", as used herein, unless otherwise indicated, includes lower alkylenyl groups, as defined above, having at least one carbon-carbon double bond, such as —$CH_2$—CH=CH—.

The term "halogen", as used herein, unless otherwise indicated, includes fluoro, chloro, bromo or iodo, such as fluoro and chloro.

The term "halogen-lower alkyl", as used herein, unless otherwise indicated, includes 1 to 6 halogen substituted alkyl, such as trifluoromethyl.

The term "lower alkyl", as used herein, unless otherwise indicated, includes 1 to 6 saturated monovalent hydrocarbon radicals having straight or branched moieties, including, but not limited to, methyl, ethyl, n-propyl, iso-propyl, n-butyl, sec-butyl, tert-butyl, and the like.

The term "lower alkenyl", as used herein, unless otherwise indicated, includes lower alkyl groups, as defined above, having at least one carbon-carbon double bond, such as —$CH_2$—$CH$=$CH_2$.

The term "lower alkynyl", as used herein, unless otherwise indicated, includes lower alkyl groups, as defined above, having at least one carbon-carbon triple bond, such as —$CH_2$— acetylene.

The term "alkoxy", as used herein, unless otherwise indicated, includes —O-lower alkyl groups wherein lower alkyl is as defined above, such as methoxy and ethoxy.

The term "alkoxyalkoxy", as used herein, unless otherwise indicated, includes —O-lower alkyl-O-lower alkyl groups wherein lower alkyl is as defined above, such as —$OCH_2CH_2OCH_3$.

The term "$C_0$–$C_6$", as used herein, unless otherwise indicated, includes zero carbon and lower alkyl wherein lower alkyl is as defined above.

The term "amino", as used herein, unless otherwise indicated, includes —$NH_2$ group, —NH-lower alkyl group, or —N(lower alkyl)$_2$ group wherein lower alkyl is as defined above, such as methylamine and dimethylamine.

The term "alkoxyamino", as used herein, unless otherwise indicated, includes —O-lower alkyl-$NH_2$ group, —O-lower alkyl-NH-lower alkyl group, or —O-lower alkyl-N(lower alkyl)$_2$ group wherein lower alkyl is as defined above, such as —$OCH_2CH_2NHCH_3$.

The term "carboxyalky", as used herein, unless otherwise indicated, includes —C(O)O— lower alkyl as an ester group wherein lower alkyl is as defined above, such as —C(O)$OCH_3$.

The term "carbonylalkyl", as used herein, unless otherwise indicated, includes —C(O)— lower alkyl as a ketone group wherein lower alkyl is as defined above, such as —C(O)$CH_3$.

The term "oxycarbonylalkyl", as used herein, unless otherwise indicated, includes —OC(O)-lower alkyl as an ester group wherein lower alkyl is as defined above, such as —OC(O)$CH_3$.

The term "carboxy", as used herein, unless otherwise indicated, includes —C(O)OH.

The term "carbonylamino", as used herein, unless otherwise indicated, includes —C(O)$NH_2$ group, —C(O)NH-lower alkyl group, or —C(O)N(lower alkyl)$_2$ as a amide group wherein lower alkyl is as defined above.

The term "oxycarbonylamino", as used herein, unless otherwise indicated, includes —OC(O)$NH_2$, —OC(O)NH-lower alkyl or —OC(O)N(lower alkyl)$_2$ as a carbamate group wherein lower alkyl is as defined above.

The term "aminocarbonylalkyl", as used herein, unless otherwise indicated, includes —NHC(O)— or —N(lower alkyl)-C(O)-lower alkyl as an amide group wherein lower alkyl is as defined above.

The term "aminocarbonyloxyalkyl", as used herein, unless otherwise indicated, includes —NHC(O)O-lower alkyl or —N(lower alkyl)-C(O)O-lower alkyl as a carbamate group wherein lower alkyl is as defined above.

The term "aminocarbonylamino", as used herein, unless otherwise indicated, includes —NHC(O)$NH_2$, —N(lower alkyl)C(O)$NH_2$, —NHC(O)NH(lower alkyl), —NHC(O)N(lower alkyl)$_2$, —N(lower alkyl)C(O)NH(lower alkyl), —N(lower alkyl)C(O)N(lower alkyl)$_2$, as an urea wherein lower alkyl is as defined above.

The term "aminosulfonylalkyl", as used herein, unless otherwise indicated, includes —NHS(O)$_2$-lower alkyl group wherein lower alkyl is as defined above.

The term "aryl", as used herein, unless otherwise indicated, includes an organic radical derived from an aromatic hydrocarbon by removal of one hydrogen, such as phenyl or naphthyl, and is unsubstituted or substituted by one, two or three substituents, selected from halogen, halogen-lower alkyl, lower alkyl, lower alkenyl, lower alkynyl, $C_0$–$C_6$cyano, $C_0$–$C_6$hydroxy, $C_0$–$C_6$alkoxy $C_0$–$C_6$alkoxyalkoxyl, $C_0$–$C_6$amino, $C_0$–$C_6$alkoxyamino, $C_0$–$C_6$carboxy, $C_0$–$C_6$carboxyalkyl, $C_0$–$C_6$carbonylamino, $C_0$–$C_6$carbonylalkyl, $C_0$–$C_6$ oxycarbonylalkyl, $C_0$–$C_6$oxycarbonylamino, $C_0$–$C_6$aminocarbonylalkyl, $C_0$–$C_6$aminocarbonyloxyalkyl, $C_0$–$C_6$aminocarbonylamino, $C_0$–$C_6$aminosulfonylalkyl, $C_0$–$C_6$cycloalkyl, $C_0$–$C_6$cycloalkenyl, $C_0$–$C_6$aryl, $C_0$–$C_6$oxyaryl, $C_0$–$C_6$alkoxyaryl, $C_0$–$C_6$aminoaryl, $C_0$–$C_6$aminoalkyaryl, $C_0$–$C_6$heterocyclyl, $C_0$–$C_6$oxyheterocyclyl, $C_0$–$C_6$alkoxyheterocyclyl, $C_0$–$C_6$aminoheterocyclyl, $C_0$–$C_6$aminoalkyheterocyclyl, $C_0$–$C_6$phenyl, $C_0$–$C_6$phenoxy, $C_0$–$C_6$phenylthio, $C_0$–$C_6$phenyl lower alkylthio, $C_0$–$C_6$sulfinyl, $C_0$–$C_6$phenyl$C_0$–$C_6$sufinyl, $C_0$–$C_6$sulfonyl, $C_0$–$C_6$phenyl$C_0$–$C_6$sulfonyl, and $C_0$–$C_6$heterocyclyl; wherein any above $C_1$–$C_6$ groups and amino groups can be optionally unsubstituted, mono-substituted or maybe disubstituted by lower alkyl; aryl includes one aromatic ring fused with an aliphatic ring, such as a saturated or partially saturated ring, such as tetrahydronaphthyl.

The term "oxyaryl", as used herein, unless otherwise indicated, includes —O-aryl group wherein aryl is as defined above.

The term "alkoxyaryl", as used herein, unless otherwise indicated, includes —O-lower alkyl-aryl group wherein lower alkyl and aryl are as defined above.

The term "aminoaryl", as used herein, unless otherwise indicated, includes amino-aryl group wherein amino and aryl are as defined above.

The term "aminoalkylaryl", as used herein, unless otherwise indicated, includes amino-lower alkyl-aryl group wherein amino, lower alkyl and aryl are as defined above.

The term "cycloalkyl", as used herein, unless otherwise indicated, includes cyclic radicals having from three to eight ring carbon atoms, including, but not limited to cyclopropyl, cyclobutyl, cyclopentyl, cyclohexyl, and the like. The cycloalkyl groups may be optionally substituted one or more times, substituents selected from the group defined above as substituents for aryl, preferably halogen, lower alkyl.

The term "cycloalkenyl", as used herein, unless otherwise indicated, includes cycloalkyl groups, as defined above, having at least one carbon-carbon double bond.

The term "heterocyclyl", as used herein, unless otherwise indicated, includes non-aromatic, single and fused rings suitably containing up to four heteroatoms in each ring, each of which independently selected from O, N and S, and which rings, may be unsubstituted or substituted independently by, for example, up to three substituents. Each heterocyclic ring suitably has from 4 to 7, preferably 5 or 6, ring atoms. A fused heterocyclic ring system may include carbocyclic rings and need include only one heterocyclic ring which may be partially saturated or saturated. The heterocyclyl includes mono, bicyclic and tricyclic heteroaromatic ring systems comprising up to four, preferably 1 or 2, heteroatoms each selected from O, N and S. Each ring may have from 4 to 7, preferably 5 or 6, ring atoms. A bicyclic or tricyclic ring system may include a carbocyclic ring. Carbocyclic ring includes cycloalkyl, cycloalkenyl or aryl ring. Examples of heterocyclyl groups include pyrrolidine, pyrrolidione, piperidine, piperidinone, piperazine, morpholine, imidazolidine, pyrazolidine, hydantoin, oxetane, tetrahydrofuran, tetrahydropyran, pyrrole, indole, pyrazole, indazole, trizole, benzotrizole, imidazole, benzoimdazole, thiophene, benzothiophene, thiozole, benzothiozole, furan, benzofuran, oxazole, benzoxazole, isoxazole, tetrazole, pyridine, pyrimidine, trizine, quinoline, isoquinoline, quinazoline, indoline, indolinone, benzotetrahydrofuran, tetrahydroquinoline, tetrahydroisoquinoline and methylenedioxyphenyl. The heterocyclic rings may be optionally substituted and substituents selected from the group defined above as substituents for aryl.

The term "oxyheterocyclyl", as used herein, unless otherwise indicated, includes —O-heterocyclyl group wherein heterocyclyl is as defined above.

The term "alkoxyheterocyclyl", as used herein, unless otherwise indicated, includes —O-lower alkyl-heterocyclyl group wherein lower alkyl and heterocyclyl are as defined above.

The term "aminoheterocyclyl", as used herein, unless otherwise indicated, includes amino-heterocyclyl group wherein amino and heterocyclyl are as defined above.

The term "aminoalkylheterocyclyl", as used herein, unless otherwise indicated, includes amino-lower alkyl-heterocyclyl group wherein amino, lower alkyl and heterocyclyl are as defined above.

A compound of formula (I) can be administered alone or in combination with one or more other therapeutic agents, possible combination therapy taking the form of fixed combinations or administration of a compound of the invention and one or more other therapeutic agents being staggered or given independently of one another, or the combined administration of fixed combinations and one or more other therapeutic agents. A compound of formula (I) can besides or in addition be administered especially for tumor therapy in combination with chemotherapy, radiotherapy, surgical intervention, or a combination of these. Long term therapy is equally possible as is adjuvant therapy in the context of other treatment strategies, as described above. Other possible treatments are therapy to maintain the patient's status after tumor regression, or even chemopreventive therapy, for example in patients at risk.

A compound according to the invention is not only for management of humans, but also for the treatment of other warm-blooded animals, for example of commercially useful animals. Such a compound may also be used as a reference standard in the test systems described above to permit a comparison with other compounds.

Salts are especially the pharmaceutically acceptable salts of compounds of formula (I). Suitable pharmaceutically acceptable salts will be apparent to those skilled in the art and include those described in *J. Pharm. Sci.,* 1977, 66, 1–19, such as acid addition salts formed with inorganic acid e.g. hydrochloric, hydrobromic, sulphuric, nitric or phosphoric acid; and organic acids e.g. succinic, maleic, acetic, fumaric, citric, tartaric, benzoic, p-toluenesulfonic, methanesulfonic or naphthalenesulfonic acid. Other salts may be used, for example in the isolation or purification of compounds of formula (I) and are included within the scope of this invention.

The compounds of this invention may be in crystalline or non-crystalline form, and, if crystalline, may optionally be hydrated or solvated. This invention includes within its scope stoichiometric hydrates as well as compounds containing variable amount of water.

The invention extents to all isomeric forms including stereoisomers and geometric isomers of the compounds of formula (I) including enantiomers and mixtures thereof e.g. racemates. The different isomeric forms may be separated or resolved one from the other by conventional methods, or any given isomer may be obtained by conventional synthetic methods or by stereospecific or asymmetric syntheses.

Those skilled in the art will recognize various synthetic methodologies that may be employed to prepare non-toxic pharmaceutically acceptable prodrugs of the compounds encompassed by Formula (I). Those skilled in the art will recognize a wide variety of non-toxic pharmaceutically acceptable solvents that may be used to prepare solvates of the compounds of the invention, such as water, ethanol, mineral oil, vegetable oil, and dimethylsulfoxide.

The compounds of general Formula (I) may be administered orally, topically, parenterally, by inhalation or spray or rectally in dosage unit formulations containing conventional non-toxic pharmaceutically acceptable carriers, adjuvants and vehicles. Oral administration in the form of a pill, capsule, elixir, syrup, lozenge, troche, or the like is particularly preferred. The term parenteral as used herein includes subcutaneous injections, intradermal, intravascular (e.g., intravenous), intramuscular, spinal, intrathecal injection or like injection or infusion techniques. In addition, there is provided a pharmaceutical formulation comprising a compound of general Formula I and a pharmaceutically acceptable carrier. One or more compounds of general Formula I may be present in association with one or more non-toxic pharmaceutically acceptable carriers and/or diluents and/or adjuvants and if desired other active ingredients. The pharmaceutical compositions containing compounds of general Formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The compounds may also be administered in the form of suppositories for rectal or vaginal administration of the drug. These compositions can be prepared by mixing the drug with a suitable non-irritating excipient which is solid at ordinary temperatures but liquid at the rectal or vaginal temperature and will therefore melt in the rectum or vagina to release the drug. Such materials include cocoa butter and polyethylene glycols.

The pharmaceutical compositions may be in the form of a sterile inject able aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered transdermally using methods know to those skilled in the art (see, for example: Chien; "transdermal Controlled Systemic Medications"; Marcel Dekker, Inc.; 1987. Lipp et al. WO 94/04157 3 Mar. 1994).

Compounds of general Formula (I) may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

For administration to non-human animals, the composition may also be added to the animal feed or drinking water. It will be convenient to formulate these animal feed and drinking water compositions so that the animal takes in an appropriate quantity of the composition along with its diet. It will also be convenient to present the composition as a premix for addition to the feed or drinking water.

For all regimens of use disclosed herein for compounds of formula I, the daily oral dosage regimen will preferably be from 0.01 to 200 mg/Kg of total body weight. The daily dosage for administration by injection, including intravenous, intramuscular, subcutaneous and parenteral injections, and use of infusion techniques will preferably be from 0.01 to 200 mg/Kg of total body weight. The daily rectal dosage regimen will preferably be from 0.01 to 200 mg/Kg of total body weight. The daily vaginal dosage regimen will preferably be from 0.01 to 200 mg/Kg of total body weight. The daily topical dosage regimen will preferably be from 0.01 to 200 mg administered between one to four times daily. The transdermal concentration will preferably be that required to maintain a daily dose of from 0.01 to 200 mg/Kg. The daily inhalation dosage regimen will preferably be from 0.01 to 200 mg/Kg of total body weight.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Preferred compounds of the invention will have certain pharmacological properties. Such properties include, but are not limited to oral bioavailability, low toxicity, low serum protein binding and desirable in vitro and in vivo half-lifes.

Assays may be used to predict these desirable pharmacological properties. Assays used to predict bioavailability include transport across human intestinal cell monolayers, including Caco-2 cell monolayers. Toxicity to cultured hepatocyctes may be used to predict compound toxicity. Penetration of the blood brain barrier of a compound in humans may be predicted from the brain levels of the compound in laboratory animals given the compound intravenously.

Serum protein binding may be predicted from albumin binding assays. Such assays are described in a review by Oravcová, et al. (Journal of Chromatography B (1996) volume 677, pages 1–27).

Compound half-life is inversely proportional to the frequency of dosage of a compound. In vitro half-lifes of compounds may be predicted from assays of microsomal half-life as described by Kuhnz and Gieschen (Drug Metabolism and Disposition, (1998) volume 26, pages 1120–1127).

In vitro receptor tyrosine kinase inhibition assay can be conducted by combining the following references:

Edwards M, International Biotechnology Lab 5 (3), 19–25, 1987

Oncogene, 1990, 5: 519–524

The Baculovirus Expression System: A Laboratory Guide, L. A. King and R. D. Possee, Chapman and Hall, 1992

Sambrook et al, 1989, Molecular cloning—A Laboratory Manual, 2nd edition, Cold Spring Harbour Laboratory Press O'Reilly et al, 1992, Baculovirus Expression Vectors—A Laboratory Manual, W. H. Freeman and Co, New York HUVEC Proliferation Assays HUVEC Cells Used in Both A and B Assays were Purchased from VEC Technologies.

A: Standard Proliferation Assay in the Presence of 10% FCS

1) Plates $10^5$ cells per well in the presence of DMEM containing 10% FCS supplemented with VEGF (100 ng/ml); 2) Allow cells to attach overnight; 3) Change the medium and include 100 nM of each compound; 4) Control wells include DMSO (vehicle); 5) Perform the assay in triplicates; 6) Change the media daily; 7) Allow the assay to proceed for four days; 8) Count the cells at the end of the assay.

B: Dose-Curve on Proliferation Assays Quantified by Uptake of Crystal Violet

1) Seed $10^4$ cells on gelatin coated wells in the presence of DMEM containing 10% FCS supplemented with VEGF (100 ng/ml); 2) Allow cells to attach four hours; 3) Change the medium to 0.5% serum supplemented with 100 ng/ml VEGF. Allow equilibration of the new media for about 16 hours; 4) Prepare dilutions of compounds in test tubes (1 nM–100 nM), so that the triplicates will indeed receive the same treatments. Control wells include DMSO (vehicle); 5) Incubate cells for 3 days, changing the compounds (media) daily; 6) At the end of the experimental procedure, wash wells with DMEM in the absence of serum three times; 7) Fix cultures in 3.7% formaldehyde for 5 min and wash with PBS; 8) Stain cell with 0.05% Crystal Violet in water (pre-filtered) for 30 min; 9) Wash cells with distilled water 3 times; 10) Drain the wells and allow them to dry; 11) Solubilize the bound dye with 0.5 ml methanol; 12) Read the plates at OD540.

All present invention compounds showed IC50 range from 10 nM–100 nM and >100 nM.

Animal Model Assays

The compounds were mixed with Tween 80 and 0.5% CMC as suspensions. Kunming male mice (19–21 g) were used. Ascitic fluid of mice HAC liver cancer was diluted with 0.9% NaCl solution (1:4), and injected 0.2 ml to each mouse subcutaneously. The whole animals (n=12) were separated evenly as test and control group randomly. The test group was administered drugs orally at 25 ml/Kg dosage once a day from second day after injection of tumor for seven days. The body weight of each animal was monitored everyday. The animals were sacrificed after ten days and each tumor was extracted and weighted for both groups and calculated the difference in percentage for antitumor activity.

The compounds were mixed with tween 80 and 0.5% CMC as suspensions. Nude female mice (17–19 g) were used. Ascitic fluid of human LOVO colon cancer was diluted with 0.9% NaCl solution (1:4), and injected 0.2 ml to each mouse subcutaneously. The whole animals (n=12) were separated even as test and control group randomly. The test group was administered drugs orally at 25 ml/Kg dosage once a day from second day after injection of tumor for eighteen days. The animals were sacrificed at 21st days and each tumor was extracted and weighted for both groups and calculated the difference in percentage for antitumor activity.

Other tumor cell line such as but not limited human A431 and human colon LS174t, in vivo animal models were similarly conducted according to above procedures.

GENERAL PREPARATIVE SUMMARY OF THE INVENTION

Representative illustrations of the preparation of the present invention are given in Schemes 1, 2, 3, 4, 5, 6 and 7.

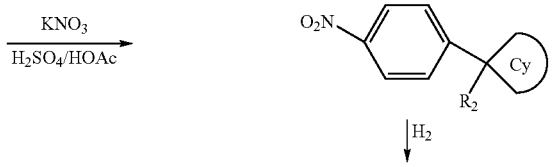

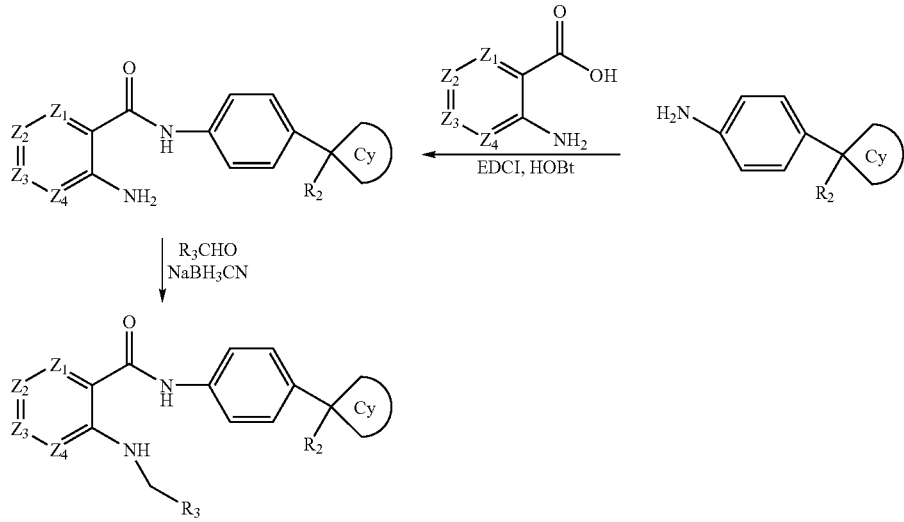

Starting material can be purchased from Aldrich and nitration by KNO$_3$ followed by regular hydrogenation to give the aniline, that can be coupled with six membered aromatic aminoacid with one equivalent EDCI [1-(3-dimethyl-aminopropyl)-3-ethylcarbodiimide hydrochloride] and HOBt (1-hydroxybenzo-triazole) to generate amino-amide. This amino-amide can be used for reductive amination with aldehyde at the presence of NaBH$_3$CN to furnish the final product.

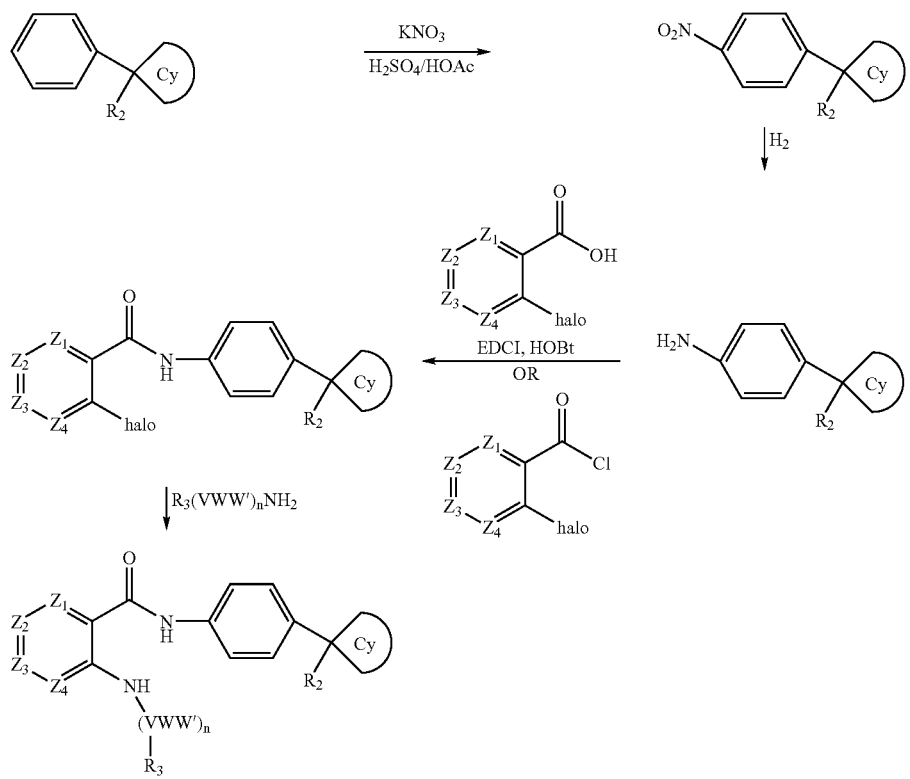

Halo-amide obtained by similar procedures described in Scheme 1 can be reacted with various amines [R$_3$(VWW')$_n$NH$_2$] product.

HOBt. Nitro compound can be hydrogenated as aniline then reduced by LAH to be amine or vice versa LAH reduction first followed by hydrogenation with the option of protection of amino group. These anilines can be converted to be the final products similarly as described in Scheme 1, 2.

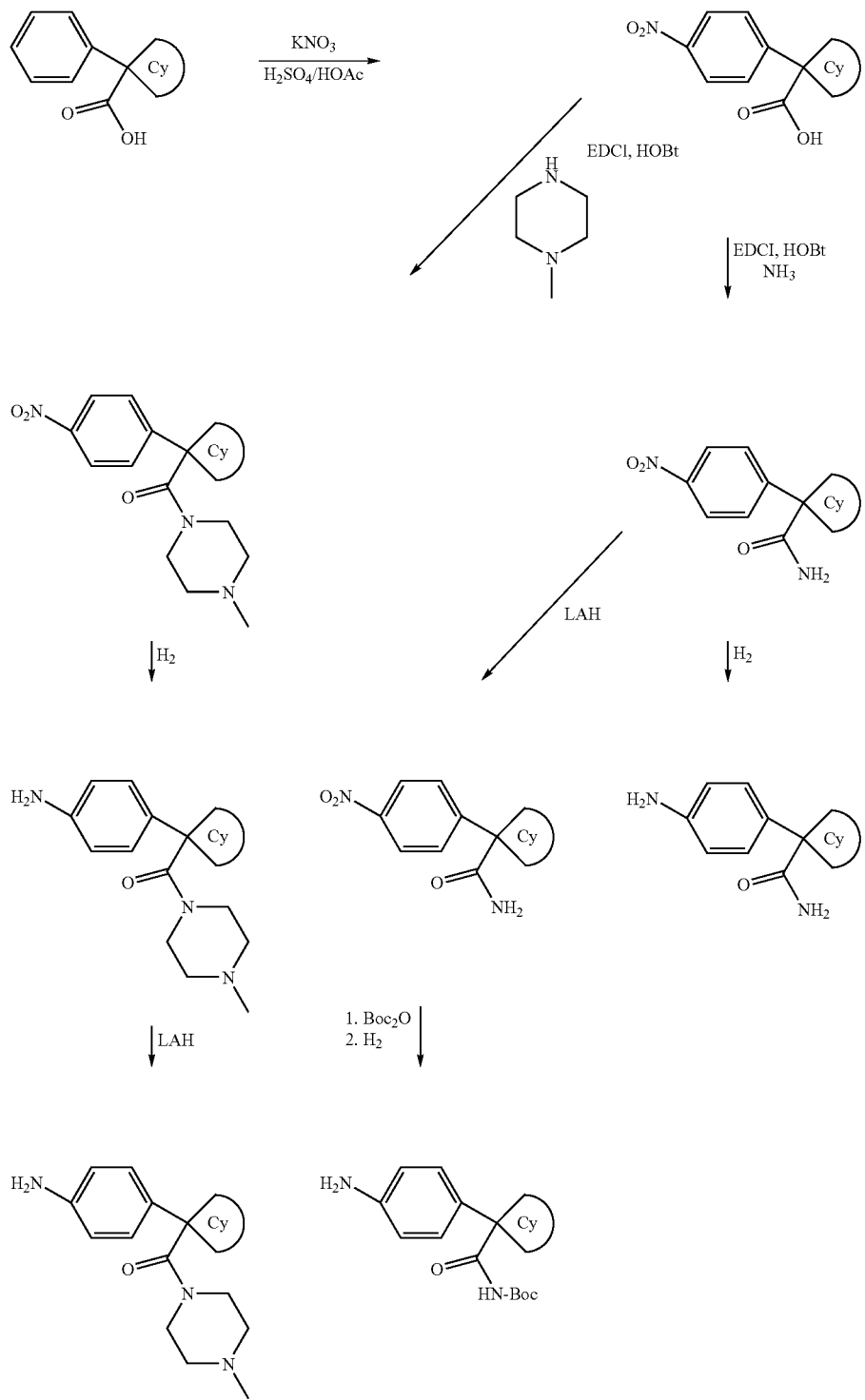

Scheme 3

Starting material can be nitrated with KNO$_3$ followed by coupling with various amines at the presence of EDCI, Scheme 4

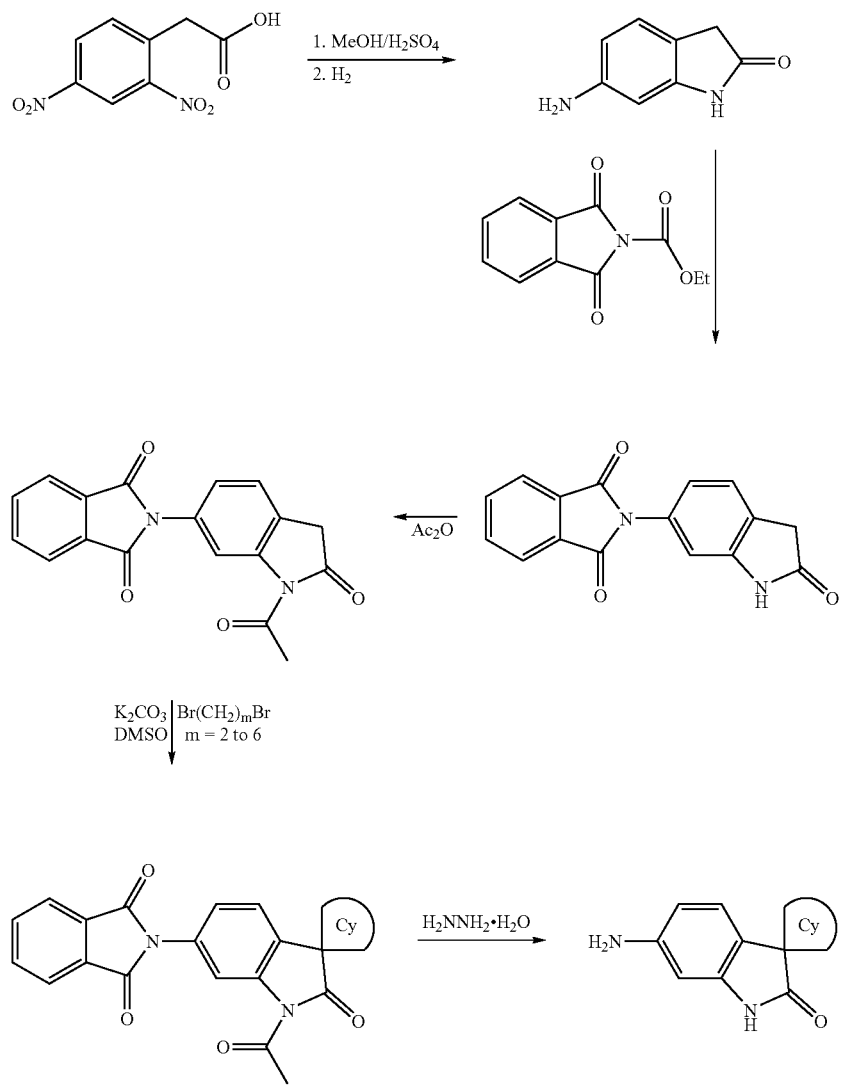

Starting material can be esterified in MeOH at acidic condition followed by hydrogenation to give a fused lactam ring. Amino group of aniline can be protected as a phthalimide and free lactam N—H can be protected with acetyl. The double protected compound can be cyclized with dihalogenalkane to form a spiro moiety and further removal of protecting groups with hydrazine to give the spiro aniline intermediate. This aniline can be converted to be the final products similarly as described in Scheme 1, 2.

Scheme 5

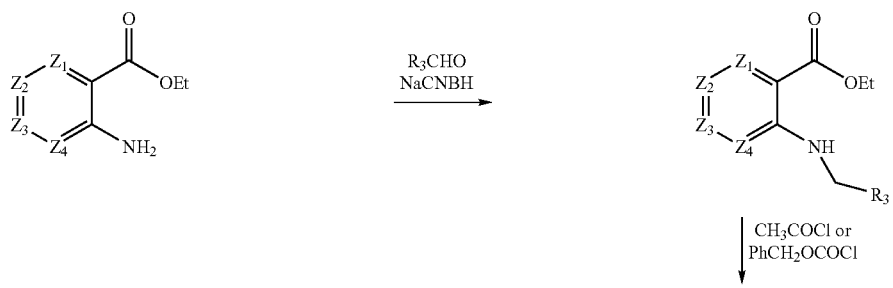

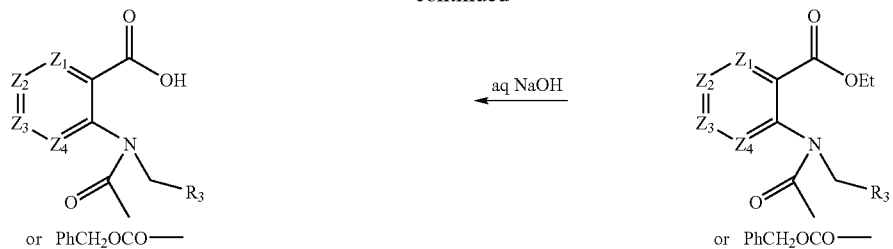

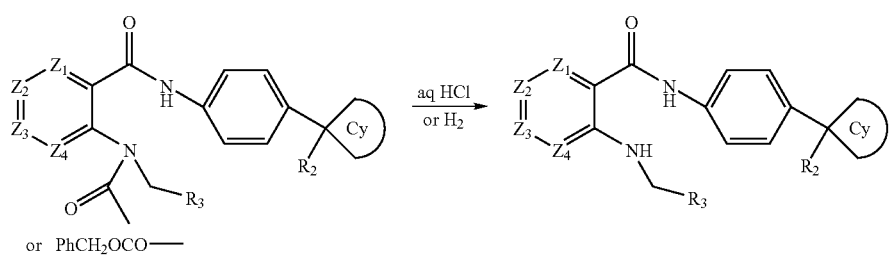

Reductive amination of starting material followed by protection of amino group with acetyl or CBZ and further hydrolysis with aqueous NaOH can give the acid. This intermediate can be coupled with the anilines made from Scheme 3, 4 to generate protected amino-amide adduct. Removal of protecting group by standard procedures gives the final product.

Scheme 6

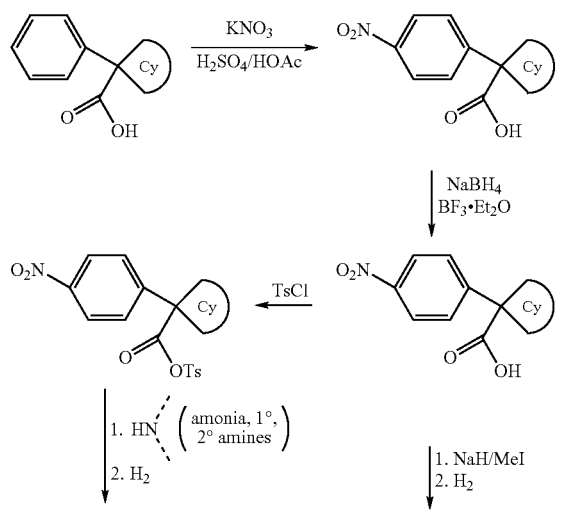

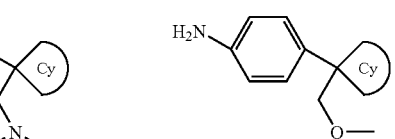

Nitro-acid compound can be reduced by $NaBH_4$/$BH_3 \cdot Et_2O$ to be an alcohol that can be activated by TsCl as a tosylate to react with various amines followed by hydrogenation to give the amino-aniline intermediate.

The alcohol can be methylated with MeI at the presence of NaH to give the methyl ether followed by hydrogenation to give the methoxy-aniline intermediate.

Above two intermediates can be used for further reactions similarly described in scheme 1, 2, 5 to furnish final products.

Scheme 7

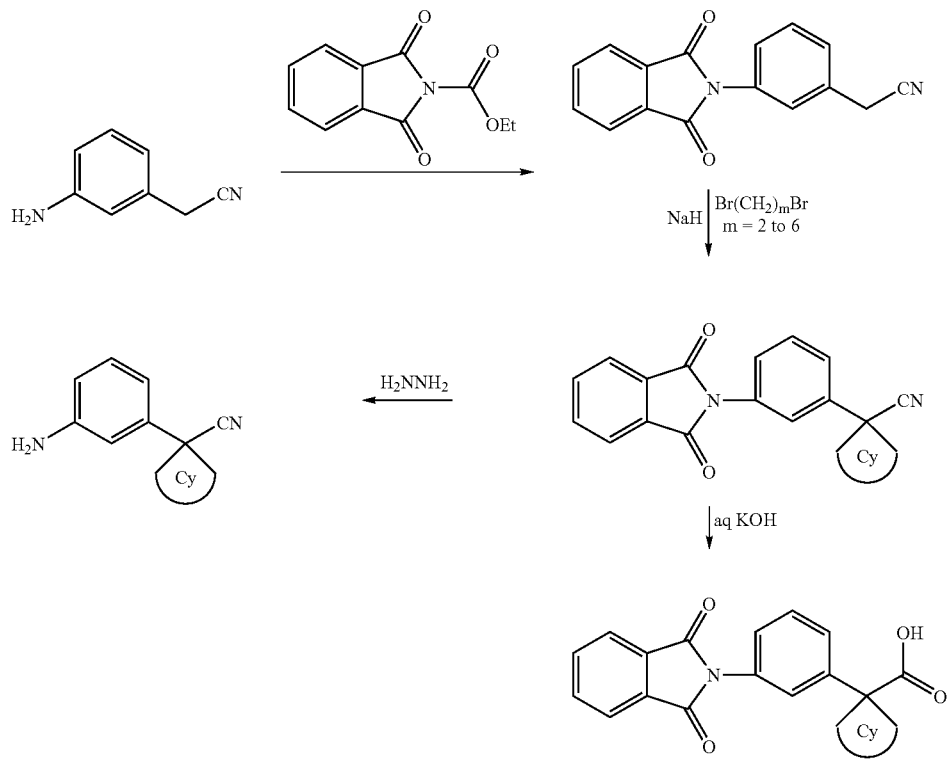

Starting material can be protected as phthalimide and cycolized with dibromoalkane followed by removal of protecting group with hydrazine. Cycolized compound can be hydrolyzed at basic condition followed by the similar procedures described in Scheme 3, 6 to functionize difference groups and deprotection to give various anilines for the syntheses of final products.

The following examples of Formula II, but not limited, can be prepared similarly according to the methods described in Scheme 1–Scheme 7.

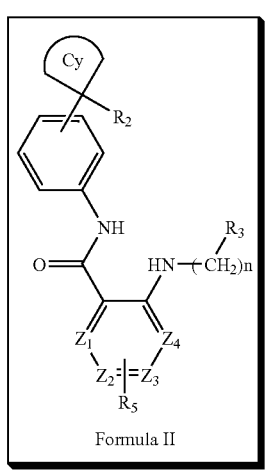

$Z_1, Z_2, Z_3 = C;$
$Z_4 = C, N$
$R_5 = H, F, Cl, CH_3$
$n = 0, 1, 2, 3$
Cy = Cyclopropyl, Cyclobutyl, Cyclopentyl, Cyclohexyl Formula II -continued $R_3$ is selected from:

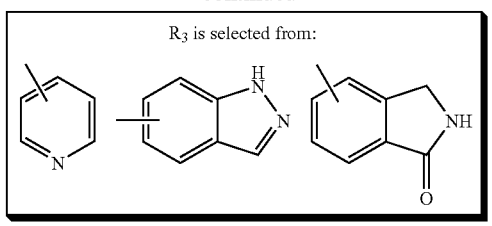

$R_2$ is selected from:

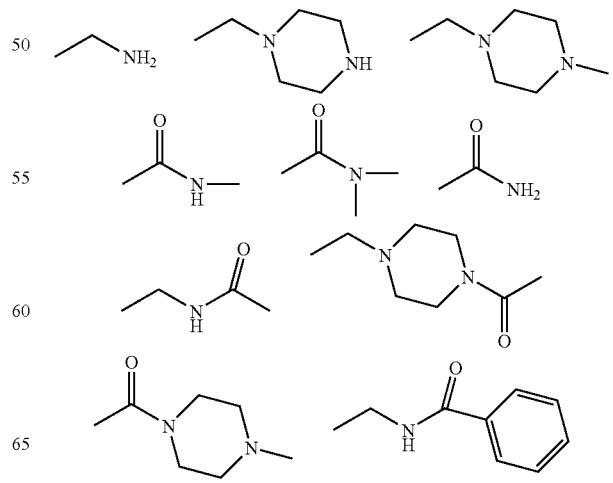

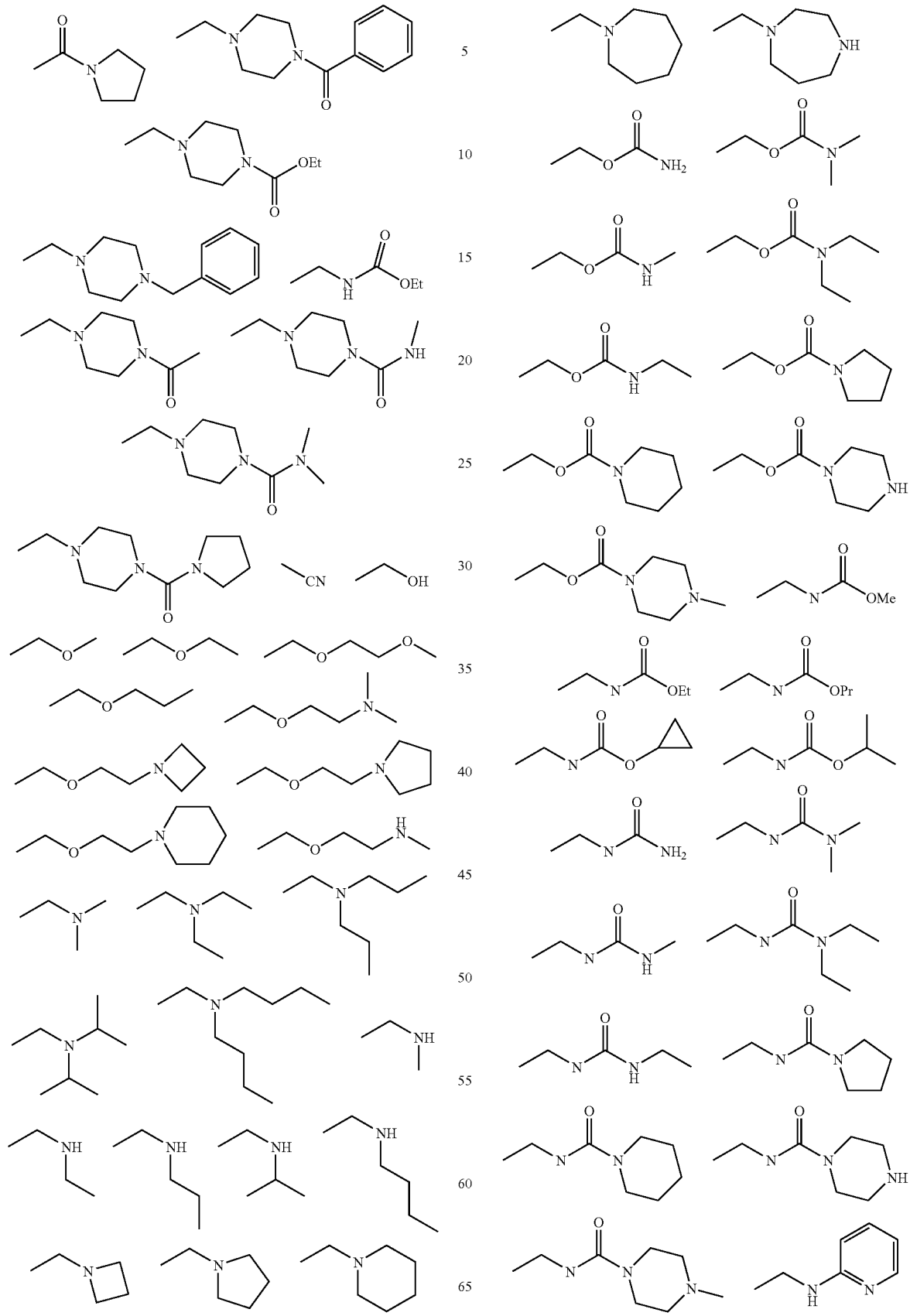

-continued

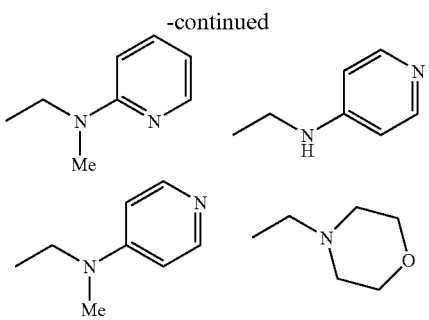

In some cases protection of certain reactive functionalities may be necessary to achieve some of above transformations. In general the need for such protecting groups will be apparent to those skilled in the art of organic synthesis as well as the conditions necessary to attach and remove such groups. Those skilled in the art will recognize that in certain instances it will be necessary to utilize different solvents or reagents to achieve some of the above transformations.

The disclosures in this application of all articles and references, including patents, are incorporated herein by reference in their entirety.

The invention is illustrated further by the following examples, which are not to be construed as limiting the invention in scope or spirit to the specific procedures described in them.

The starting materials are and various intermediates may be obtained from commercial sources, prepared from commercially available organic compounds, or prepared using well know synthetic methods.

Representative methods for preparing intermediates of the invention are set forth below in the examples.

The following abbreviation have been used and others are all standard chemical formula representation.

| EtOH: | ethanol | RT: | room temperature |
|---|---|---|---|
| TEA: | triethylamine | DIEA: | diisopropylethyl- amine |
| EDCI: | 1-(3-dimethylaminopropyl)- 3-ethylcarbodiimide hydro- chloride | EtOAc: | ethyl acetate |
| | | DMF: | N,N-dimethylformamide |
| HOBt: | 1-hydroxybenzotriazole hydrate | g: | gram, ml: milliliter |
| | | TLC: | thin layer chromato- graphy |
| THF: | tetrahydrofuran | | |
| DMSO: | dimethylsulfoxide | | |
| eq: | equivalent, | | |
| MeI: | methyl iodide | | |

EXAMPLE 1

N-[4-(cyanocyclobutyl)-phenyl]{2-[(4-pyridylmethyl)amino]phenyl}carboxamide

A: 1-(4-aminophenyl)cyclobutanecarbonitrile

A mixture of 1-phenylcyclobutanecarbonitrile (5 g) and acetic acid (15 ml) and $H_2SO_4$ (10 ml) and $KNO_3$ (1.1 eq) was stirred at 0° C. for 20 min. The mixture was warmed to RT and stirred for two hours. The mixture was poured on ice and stirred until all ice melted. The precipitate was filtered and recrystalized from EtOH to give 1-(4-nitrophenyl)-cyclobutanecarbonitrile. The above product (2 g) was mixed with Pd—C (10%, 800 mg) in EtOH (100 ml) and hydrogenated under $H_2$ atmosphere for 1 hour. The reaction was filtered through Celite and evaporated to give 1-(4-aminophenyl)-cyclobutanecarbonitrile, Mass: (M+1) 172, which was used for next step without further purification.

B: N-[4-(cyanocyclobutyl)-phenyl]{2-[(4-pyridylmethyl)amino]phenyl}carboxamide

A mixture of anthranilic acid (1.4 g) and 1-(4-aminophenyl)cyclobutane-carbonitrile (1 eq) and TEA (1.2 eq) in dichloromethane (80 ml) was stirred with EDCI (1.25 eq) and HOBt (1 eq) at RT overnight. The reaction was washed with sat. $NaHCO_3$, $H_2O$ followed by brine, dried over $Na_2SO_4$ and evaporated. The residue was purified by column chromatography to give (2-aminophenyl)-N-[4-(cyanocyclobutyl)phenyl]-carboxamide.

C: N-[4-(cyanocyclobutyl)-phenyl]{2-[(4-pyridylmethyl)amino]phenyl}carboxamide

The above compound (400 mg) was mixed with 4-pyridylformaldehyde (1.2 eq) and $NaBH_3CN$ (2 eq) in methanol and stirred overnight. The solvent was evaporated, and EtOAc (80 ml) and $H_2O$ (80 ml) were added. The solution was extracted with EtOAc and washed with $H_2O$ followed by brine, dried over $Na_2SO_4$ and evaporated. The residue was purified by column chromatography to give title compound. Mass: (M+1), 383.

EXAMPLE 2

N-[4-(cyanocyclopropyl)-phenyl]{2-[(4-pyridylmethyl)amino]phenyl}carboxamide

The title compound was prepared by similar manner to Example 1, starting from 1-phenylcyclopropylcarbonitrile. Mass: (M+1), 369.

EXAMPLE 3

N-[4-(cyanocyclopentyl)-phenyl]{2-[(4-pyridylmethyl)amino]phenyl}carboxamide

The title compound was prepared by similar manner to Example 1, starting from 1-phenylcyclopentylcarbonitrile. Mass: (M+1), 397.

EXAMPLE 4

N-[4-(cyanocyclohexyl)-phenyl]{2-[(4-pyridylmethyl)amino]phenyl}carboxamide

The title compound was prepared by similar manner to Example 1, starting from 1-phenylcyclohexylcarbonitrile. Mass: (M+1), 411.

EXAMPLE 5

N-[4-(cyanocyclobutyl)phenyl]{2-[(4-pyridylmethyl)amino](3-pyridyl)}carboxamide

A mixture of 2-chloronicotinoyl chloride (50 mg) and 1-(4-aminophenyl)cyclobutanecarbonitrile (1 eq) and $K_2CO_3$ (80 mg) in dichloromethane (20 ml) was stirred at RT for 30 min. The reaction was filtered and the filtrate was evaporated. The residue was mixed with 4-pyridylmethylamine (120 mg) in pentanol (10 ml) and heated at 120° C. for 4 hours. The reaction was evaporated with silica-gel (1 g) and purified by column chromatography to give title compound. Mass: (M+1), 384.

EXAMPLE 6

N-[4-(cyanocyclopropyl)-phenyl]{2-[(4-pyridylmethyl)amino](3-pyridyl)}carboxamide The title compound was prepared by similar manner to Example 5, starting from 1-phenylcyclopropylcarbonitrile. Mass: (M+1), 370.

EXAMPLE 7

N-[4-(cyanocyclopentyl)-phenyl]{2-[(4-pyridylmethyl)amino](3-pyridyl)}carboxamide The title compound was prepared by similar manner to Example 5, starting from 1-phenylcyclopentylcarbonitrile. Mass: (M+1), 398.

EXAMPLE 8

N-[4-(cyanocyclohexyl)-phenyl]{2-[(4-pyridylmethyl)amino](3-pyridyl)}carboxamide The title compound was prepared by similar manner to Example 5, starting from 1-phenylcyclohexylcarbonitrile. Mass: (M+1), 412.

EXAMPLE 9

N-{4-[(methoxymethyl)cyclobutyl]phenyl}{2-[(4-pyridylmethyl)amino]phenyl}-carboxamide Method 1:

A: [(4-Nitrophenyl)cyclobutyl]methane-1-ol

A mixture of 1-phenylcyclobutanecarboxylic acid (10) and acetic acid (20 ml) and H$_2$SO$_4$ (20 ml) and KNO$_3$ (1.1 eq) was stirred at 0° C. for 20 min. The mixture was warmed to RT and stirred overnight. The mixture was poured on ice and stirred until all ice melted. The precipitate was filtered and used for next step without further purification. The above product (5 g) was dissolved into THF and stirred at 0° C., NaBH$_4$ (3 eq) was added slowly to the reaction followed by slowly addition of BF$_3$.Et$_2$O (3 eq). The reaction was stirred at RT overnight and quenched with 1 N NaOH slowly until bubble ceased. The solution was extracted with EtOAc and washed with H$_2$O followed by brine, dried over Na$_2$SO$_4$ and evaporated. The residue was purified by column chromatography to give [(4-nitrophenyl)cyclobutyl]methane-1-ol as an oil.

B: 4-[(methoxymethyl)cyclobutyl]phenylamine

A mixture of [(4-nitrophenyl)cyclobutyl]methane-1-ol (500 mg) and NaH (60% in mineral oil, 1.2 eq) and MeI (1.2 eq) in THF was stirred at RT overnight then quenched with H$_2$O. The solution was extracted with EtOAc and washed with H$_2$O followed by brine, dried over Na$_2$SO$_4$ and evaporated. The residue was mixed with Pd—C (10%, 100 mg) in EtOH (50 ml) and hydrogenated under H$_2$ atmosphere for 30 min. The reaction was filtered through Celite and evaporated to give 4-[(methoxymethyl)cyclobutyl]phenylamine which used for next step without further purification.

The title compound was prepared by similar manner to Example 1, starting from 4-[(methoxymethyl)cyclobutyl]phenyl-amine. Mass: (M+1), 402.

Method 2:

A: Ethyl 2-[N-(4-pyridyl-methyl)acetylamino]benzoate

A mixture of ethyl 2-aminobenzoate (4 g) and 4-pyridyl-formaldehyde (1.2 eq) and NaBH$_3$CN (2 eq) in methanol stirred overnight. The solvent was evaporated, and EtOAc (100 ml) and H$_2$O (100 ml) were added. The solution was extracted three times with EtOAc and washed with H$_2$O followed by brine, dried over Na$_2$SO$_4$ and evaporated. The residue was purified by column chromatography to give ethyl 2-[(4-pyridylmethyl)-amino]benzoate. The above compound (400 mg) was stirred with acetyl chloride (1.2 eq) and DIEA (1.2 eq) in dichloromethane at RT for two hours. The solution was washed with H$_2$O followed by brine, dried over Na$_2$SO$_4$ and evaporated to give ethyl 2-[N-(4-pyridyl-methyl)acetylamino]benzoate for next step without further purification.

B: N-[2-(N-{4-[(methoxymethyl)cyclopropyl]phenyl}carbamoyl)phenyl]-N-(4-pyridylmethyl)acetamide A mixture of ethyl 2-[N-(4-pyridyl-methyl)acetylamino]benzoate (300 mg) and 5 N NaOH (2 ml) in EtOH (20 ml) was stirred at RT for three hours. The solution was neutralized with 5 N HCl and evaporated to dryness. The residue was washed with methanol and filtered. The filtrate was evaporated and the residue was mixed with 4-[(methoxymethyl)cyclobutyl]phenylamine (1 eq), EDCI (1.25 eq), HOBt (1 eq) and DIEA (1.25 eq) in DMF (10 ml) and stirred overnight. The solution was mixed with dichloromethane (80 ml) and washed with water three times followed by brine, dried over Na$_2$SO$_4$ and evaporated, further purified by preparative TLC to give N-[2-(N-{4-[(methoxymethyl)-cyclopropyl]phenyl}carbamoyl)phenyl]-N-(4-pyridylmethyl)-acetamide C: N-{4-[(methoxymethyl)cyclobutyl]phenyl}{2-[(4-pyridylmethyl)amino]phenyl}-carboxamide A mixture of N-[2-(N-{4-[(methoxymethyl)-cyclopropyl]phenyl}carbamoyl)-phenyl]-N-(4-pyridylmethyl)acetamide (100 mg) and 20% HCl (5 ml) in EtOH (15 ml) was stirred at 80° C. overnight. The solution was basified with NaHCO$_3$ and evaporated with silica gel and purified by column chromatography to give the title compound. Mass: (M+1), 402.

EXAMPLE 10

N-{4-[(methoxymethyl)cyclobutyl]phenyl}{2-[(4-pyridylmethyl)amino](3-pyridyl)}carboxamide The title compound was prepared by similar manner to Example 5, starting from 4-[(methoxymethyl)cyclobutyl]phenylamine. Mass: (M+1), 403.

EXAMPLE 11

N-{4-[(hydroxymethyl)cyclobutyl]phenyl}{2-[(4-pyridylmethyl)amino]phenyl}carboxamide A mixture of [(4-nitrophenyl)cyclobutyl]methane-1-ol (500 mg) was mixed with Pd—C (10%, 80 mg) in EtOH (100 ml) and hydrogenated under H$_2$ atmosphere for 1 hour. The reaction was filtered through Celite and evaporated to give [(4-aminophenyl)cyclobutyl]methane-1-ol.

The title compound was prepared by similar manner to Example 1, starting from [(4-aminophenyl)cyclobutyl]methane-1-ol. Mass: (M+1), 388.

EXAMPLE 12

N-{4-[(hydroxymethyl)cyclobutyl]phenyl}{2-[(4-pyridylmethyl)amino](3-pyridyl)}carboxamide The title compound was prepared by similar manner to Example 5, starting from [(4-aminophenyl)cyclobutyl]methane-1-ol. Mass: (M+1), 389.

EXAMPLE 13

N-{4-[(methoxymethyl)cyclopentyl]phenyl}{2-[(4-pyridylmethyl)amino](3-pyridyl)}carboxamide The title compound was prepared by similar manner to Example 5, starting from 4-[(methoxymethyl)cyclopentyl]phenylamine. Mass: (M+1), 417.

EXAMPLE 14

N-{4-[(methoxymethyl)cyclohexyl]phenyl}{2-[(4-pyridylmethyl)amino](3-pyridyl)}carboxamide The title compound was prepared by similar manner to Example 5, starting from 4-[(methoxymethyl)cyclohexyl]phenylamine. Mass: (M+1), 431.

EXAMPLE 15

N-(7-oxospiro[cyclopentane-1,3'-indoline]-11-yl){2-[(4-pyridylmethyl)amino]phenyl}carboxamide A: 6-Aminoindolin-2-one A mixture of 2,4-dinitrophenylacetic acid (10 g) and $H_2SO_4$ (0.1 eq) in EtOH (300 ml) was refluxed overnight. The solvent was evaporated, and EtOAc (150 ml) and $H_2O$ (200 ml) were added. The solution was extracted three times with EtOAc and washed with $H_2O$ followed by brine, dried over $Na_2SO_4$ and evaporated to give ethyl 2-(2,4-dinitrophenyl)acetate for next step without further purification. The above compound (5 g) was mixed with Pd—C (10%, 500 mg) in EtOH (200 ml) and hydrogenated under $H_2$ atmosphere overnight. The reaction was filtered through Celite and evaporated. The residue was washed with EtOAc and filtered to give 6-aminoindolin-2-one.

B: 1-Acetyl-6-(1,3-dioxobenzo[c]azolidin-2-yl)-2-oxoindoline

A mixture of above compound (2 g) and ethyl 1,3-dioxobenzo[c]azolidine-2-carboxylate (1.1 eq) in THF was refluxed overnight. The reaction was cooled and the precipitate was filtered. The gray solid (2 g) was heated with acetic anhydride (2 eq) in acetic acid (40 ml) at 115° C. overnight. The solvent was evaporated and the product was triturated with 50% EtOAc/Hexane and filtered to give 1-acetyl-6-(1,3-dioxobenzo[c]-azolidin-2-yl)-2-oxoindoline as a dark gray solid.

C: 11-Aminospiro[cyclopentane-1,3'-indoline]-7-one

A mixture of 1-acetyl-6-(1,3-dioxobenzo[c]azolidin-2-yl)-2-oxoindoline (500 mg) and $K_2CO_3$ (1.5 eq) and dibromobutane (1.3 eq) in DMSO (10 ml) was stirred at RT overnight. The solution was mixed with EtOAc (100 ml) and $H_2O$ (100 ml) and extracted with EtOAc three times and washed with $H_2O$ followed by brine, dried over $Na_2SO_4$ and evaporated to give 6-acetyl-11-(1,3-dioxobenzo[c]azolidin-2-yl)-7-oxospiro[cyclopean-tane-1,3'-indoline]which was used for next step without further purification. Mass: (M+1), 375.

A mixture of above product (200 mg) and $H_2NNH_2.H_2O$ (2 eq) in methanol was stirred at RT for 1 hour. The solvent was evaporated, and EtOAc (80 ml) and 1 N NaOH (50 ml) were added. The solution was extracted three times with EtOAc and washed with $H_2O$ followed by brine, dried over $Na_2SO_4$ and evaporated. The residue was purified by column chromatography to give 11-aminospiro[cyclopentane-1,3'-indoline]-7-one. Mass: (M+1), 203

The title compound was prepared by similar manner to Example 1, starting from 11-aminospiro[cyclopentane-1,3'-indoline]-7-one. Mass: (M+1), 413.

EXAMPLE 16

N-(7-oxospiro[cyclopentane-1,3'-indoline]-11-yl){2-[(4-pyridylmethyl)amino]-phenyl}carboxamide The title compound was prepared by similar manner to Example 5, starting from 11-aminospiro[cyclopentane-1,3'-indoline]-7-one. Mass: (M+1), 414.

EXAMPLE 17

N-(5-oxospiro[cyclopropane-1,3'-indoline]-9-yl){2-[(4-pyridylmethyl)amino]-phenyl}carboxamide The title compound was prepared by similar manner to Example 13 and Example 1, starting from 9-aminospiro[cyclopropane-1,3'-indoline]-5-one. Mass: (M+1), 385.

EXAMPLE 18

N-(5-oxospiro[cyclopropane-1,3'-indoline]-9-yl){2-[(4-pyridylmethyl)amino](3-pyridyl)}-carboxamide The title compound was prepared by similar manner to Example 13 and Example 5, starting from 9-aminospiro[cyclopropane-1,3'-indoline]-5-one. Mass: (M+1), 386.

EXAMPLE 19

N-[4-(cyanocyclopentyl)phenyl][2-(1H-indazol-6-ylamino)(3-pyridyl)]carboxamide

A mixture of 2-chloronicotinoyl chloride (50 mg) and 1-(4-aminophenyl)-cyclopentanecarbonitrile (1 eq) and $K_2CO_3$ (80 mg) in dichloromethane (20 ml) was for 30 min. The reaction was filtered and the filtrate was evaporated. The residue was mixed with 6-aminoindazole (150 mg) neat and heated at 210° C. for 2 hour. The reaction was cooled and purified by column chromatography to give the title compound. Mass: (M+1), 423.

The invention claimed is:

1. Six membered amino-amide compound of formula (I)

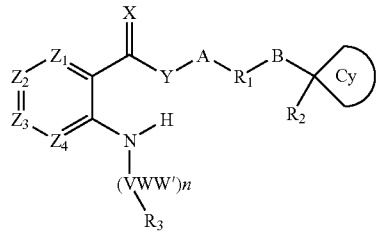

Formula (I)

Wherein
X is O or S;
Y is —N($R_4$)—;
$Z_1$, $Z_2$, $Z_3$ and $Z_4$ are independently $CR_5$ or N;
A is selected from direct bond, lower alkylenyl and lower alkenlenyl;
B is selected from direct bond, lower alkylenyl, lower alkenlenyl, —O—, —N($R_4$)—, —C(O)N($R_4$)—, —OC(O)N($R_4$)—, —N($R_4$)C(O)—, —N($R_4$)C(O)O—, —N($R_4$)C(O)N($R_4$)—, —C(O)—, —S(O)—, —S(O)$_2$—, —S(O)N($R_4$)—, —S(O)$_2$N($R_4$)—, —N($R_4$)S(O)—, —N($R_4$)S(O)$_2$—, —N($R_4$)S(O)N($R_4$)—, —N($R_4$)S(O)$_2$N($R_4$)—;
$R_1$ is selected from cycloalkyl, cycloalkenyl, aryl and heterocyclyl;
Cy is selected from cycloalkyl, cycloalkenyl and heterocyclyl;
$R_2$ is selected from halogen-lower alkyl, lower alkyl, lower alkenyl, lower alkynyl, $C_0$–$C_6$cyano, $C_0$–$C_6$hydroxy, $C_0$–$C_6$alkoxy, $C_0$–$C_6$alkoxyalkoxyl, $C_0$–$C_6$amino, $C_0$–$C_6$alkoxyamino, $C_0$–$C_6$carboxy, $C_0$–$C_6$carboxyalkyl, $C_0$–$C_6$carbonylamino, $C_0$–$C_6$carbonylalkyl, $C_0$–$C_6$oxycarbonylalkyl, $C_0$–$C_6$oxycarbonylamino, $C_0$–$C_6$aminocarbonylalkyl, $C_0$–$C_6$aminocarbonyloxyalkyl, $C_0$–$C_6$aminocarbonylamino, $C_0$–$C_6$aminosulfonylalkyl, $C_0$–$C_6$cycloalkyl, $C_0$–$C_6$cycloalkenyl, $C_0$–$C_6$aryl, $C_0$–$C_6$oxyaryl, $C_0$–$C_6$alkoxyaryl, $C_0$–$C_6$aminoaryl, $C_0$–$C_6$aminoalkylaryl, $C_0$–$C_6$heterocyclyl, $C_0$–$C_6$oxyheterocyclyl, $C_0$–$C_6$alkoxyheterocyclyl, $C_0$–$C_6$aminoheterocyclyl and $C_0$–$C_6$aminoalkylheterocyclyl; wherein any above $C_1$–$C_6$ groups and amino groups can be optionally unsubstituted, mono-substituted or possibly disubstituted by lower alkyl;
$R_1$ and $R_2$ are combined together as a fused spiro ring G comprising C, N, O or S, wherein ring G is selected from cycloalkyl, cycloalkenyl, aryl and heterocyclyl, which can be saturated or partially saturated and unsubstituted mono or polysubstituted;
V is C, N or SO$_2$;
W and W' are independently of each other hydrogen, halogen or lower alkyl; or together with the carbon atom to form a cycloalkyl, a cycloalkenyl, or a heterocyclyl ring;
n is an integer from 0 to 6;
$R_3$ is a heterocyclyl or an aryl;
$R_4$ is H or a lower alkyl;
$R_5$ is H, halogen or lower alkyl;
or of a N-oxide or a possible tautomer thereof;
or a pharmaceutically acceptable salt thereof.

2. A compound of Formula (I) according to claim 1, wherein.
X is O or S;
Y is —NH—;
$Z_1$, $Z_2$, $Z_3$ and $Z_4$ are independently $CR_5$ or N;
A is selected from direct bond, lower alkylenyl and lower alkenlenyl;
B is selected from direct bond, lower alkylenyl, lower alkenlenyl, —O—, —N($R_4$)—, —C(O)N($R_4$)—, —OC(O)N($R_4$)—, —N($R_4$)C(O)—, —N($R_4$)C(O)O—, —N($R_4$)C(O)N($R_4$)—, —C(O)—, —S(O)—, —S(O)$_2$—, —S(O)N($R_4$)—, —S(O)$_2$N($R_4$)—, —N($R_4$)S(O)—, —N($R_4$)S(O)$_2$—, —N($R_4$)S(O)N($R_4$)—, —N($R_4$)S(O)$_2$N($R_4$)—;
$R_1$ is selected from cycloalkyl, cycloalkenyl, aryl and heterocyclyl;
Cy is selected from cycloalkyl, cycloalkenyl and heterocyclyl;
$R_2$ is selected from halogen-lower alkyl, lower alkyl, lower alkenyl, lower alkynyl, $C_0$–$C_6$cyano, $C_0$–$C_6$hydroxy, $C_0$–$C_6$alkoxy, $C_0$–$C_6$alkoxyalkoxyl, $C_0$–$C_6$amino, $C_0$–$C_6$alkoxyamino, $C_0$–$C_6$carboxy, $C_0$–$C_6$carboxyalkyl, $C_0$–$C_6$carbonylamino, $C_0$–$C_6$carbonylalkyl, $C_0$–$C_6$oxycarbonylalkyl, $C_0$–$C_6$oxycarbonylamino, $C_0$–$C_6$aminocarbonylalkyl, $C_0$–$C_6$aminocarbonyloxyalkyl, $C_0$–$C_6$aminocarbonylamino, $C_0$–$C_6$aminosulfonylalkyl, $C_0$–$C_6$cycloalkyl, $C_0$–$C_6$cycloalkenyl, $C_0$–$C_6$aryl, $C_0$–$C_6$oxyaryl, $C_0$–$C_6$alkoxyaryl, $C_0$–$C_6$aminoaryl, $C_0$–$C_6$aminoalkyaryl, $C_0$–$C_6$heterocyclyl, $C_0$–$C_6$oxyheterocyclyl, $C_0$–$C_6$alkoxyheterocyclyl, $C_0$–$C_6$aminoheterocyclyl and $C_0$–$C_6$aminoalkylheterocyclyl; wherein any above $C_1$–$C_6$groups and amino groups can be optionally unsubstituted, mono-substituted or possibly disubstituted by lower alkyl;
$R_1$ and $R_2$ are combined together as a fused spiro ring G comprising C, N, O or S, wherein ring G is selected from cycloalkyl, cycloalkenyl, aryl and heterocyclyl, which can be saturated or partially saturated and unsubstituted, mono or polysubstituted;
V is C, N or SO$_2$;
W and W' are independently of each other hydrogen, halogen or lower alkyl; or together with the carbon atom to form a cycloalkyl, a cycloalkenyl, or a heterocyclyl ring;
n is an integer from 0 to 6;
$R_3$ is a heterocyclyl or an aryl;
$R_4$ is H or a lower alkyl;
$R_5$ is H, halogen or lower alkyl;
or of a N-oxide or a possible tautomer thereof;
or a pharmaceutically acceptable salt thereof.

3. A compound of Formula (I) according to claim 1, wherein
X is O or S;
Y is —NH—;
$Z_1$, $Z_2$, $Z_3$ and $Z_4$ are independently $CR_5$ or N;
A is direct bond;
B is direct bond;
$R_1$ is selected from cycloalkyl, cycloalkenyl, aryl and heterocyclyl;
Cy is selected from cycloalkyl, cycloalkenyl and heterocyclyl;
$R_2$ is selected from halogen-lower alkyl, lower alkyl, lower alkenyl, lower alkynyl, $C_0$–$C_6$cyano, $C_0$–$C_6$hydroxy, $C_0$–$C_6$alkoxy, $C_0$–$C_6$alkoxyalkoxyl, $C_0$–$C_6$amino, $C_0$–$C_6$alkoxyamino, $C_0$–$C_6$carboxy, $C_0$–$C_6$carboxyalkyl, $C_0$–$C_6$carbonylamino, $C_0$–$C_6$carbonylalkyl, $C_0$–$C_6$oxycarbonylalkyl, $C_0$–$C_6$oxycarbonylamino, $C_0$–$C_6$aminocarbonylalkyl, $C_0$–$C_6$aminocarbonyloxyalkyl, $C_0$–$C_6$aminocarbonylamino, $C_0$–$C_6$aminosulfonylalkyl, $C_0$–$C_6$cycloalkyl, $C_0$–$C_6$cycloalkenyl, $C_0$–$C_6$aryl, $C_0$–$C_6$oxyaryl, $C_0$–$C_6$alkoxyaryl, $C_0$–$C_6$aminoaryl, $C_0$–$C_6$aminoalkylaryl, $C_0$–$C_6$heterocyclyl, $C_0$–$C_6$oxyheterocyclyl, $C_0$–$C_6$alkoxyheterocyclyl, $C_0$–$C_6$aminoheterocyclyl and $C_0$–$C_6$aminoalkylheterocyclyl; wherein any above $C_1$–$C_6$ groups and amino groups can be optionally unsubstituted, mono-substituted or possibly disubstituted by lower alkyl;

$R_1$ and $R_2$ are combined together as a fused spiro ring G comprising C, N, O or S, wherein ring G is selected from cycloalkyl, cycloalkenyl, aryl and heterocyclyl, which can be saturated or partially saturated and unsubstituted, mono or polysubstituted;

V is C, N or $SO_2$;

W and W' are independently of each other hydrogen, halogen or lower alkyl; or together with the carbon atom to form a cycloalkyl, a cycloalkenyl, or a heterocyclyl ring;

n is an integer from 0 to 6;

$R_3$ is a heterocyclyl or an aryl;

$R_4$ is H or a lower alkyl;

$R_5$ is H, halogen or lower alkyl;

or of a N-oxide or a possible tautomer thereof;

or a pharmaceutically acceptable salt thereof.

4. A compound of Formula (I) according to claim 1, wherein

X is O or S;

Y is —NH—;

$Z_1$, $Z_2$, $Z_3$ and $Z_4$ are independently $CR_5$ or N;

A is direct bond;

B is direct bond;

$R_1$ is aryl or heterocyclyl;

Cy is selected from cycloalkyl, cycloalkenyl and heterocyclyl;

$R_2$ is selected from halogen-lower alkyl, lower alkyl, lower alkenyl, lower alkynyl, $C_0$–$C_6$cyano, $C_0$–$C_6$hydroxy, $C_0$–$C_6$alkoxy, $C_0$–$C_6$alkoxyalkoxyl, $C_0$–$C_6$amino, $C_0$–$C_6$alkoxyamino, $C_0$–$C_6$carboxy, $C_0$–$C_6$carboxyalkyl, $C_0$–$C_6$carbonylamino, $C_0$–$C_6$carbonylalkyl, $C_0$–$C_6$oxycarbonylalkyl, $C_0$–$C_6$oxycarbonylamino, $C_0$–$C_6$aminocarbonylalkyl, $C_0$–$C_6$aminocarbonyloxyalkyl, $C_0$–$C_6$aminocarbonylamino, $C_0$–$C_6$aminosulfonylalkyl, $C_0$–$C_6$cycloalkyl, $C_0$–$C_6$cycloalkenyl, $C_0$–$C_6$aryl, $C_0$–$C_6$oxyaryl, $C_0$–$C_6$alkoxyaryl, $C_0$–$C_6$aminoaryl, $C_0$–$C_6$aminoalkylaryl, $C_0$–$C_6$heterocyclyl, $C_0$–$C_6$oxyheterocyclyl, $C_0$–$C_6$alkoxyheterocyclyl, $C_0$–$C_6$aminoheterocyclyl and $C_0$–$C_6$aminoalkylheterocyclyl; wherein any above $C_1$–$C_6$ groups and amino groups can be optionally unsubstituted, mono-substituted or possibly disubstituted by lower alkyl;

$R_1$ and $R_2$ are combined together as a fused spiro ring G comprising C, N, O or S, wherein ring G is selected from cycloalkyl, cycloalkenyl, aryl and heterocyclyl, which can be saturated or partially saturated and unsubstituted, mono or polysubstituted;

V is C, N or $SO_2$;

W and W' are independently of each other hydrogen, halogen or lower alkyl; or together with the carbon atom to form a cycloalkyl, a cycloalkenyl, or a heterocyclyl ring;

n is an integer from 0 to 6;

$R_3$ is a heterocyclyl or an aryl;

$R_4$ is H or a lower alkyl;

$R_5$ is H, halogen or lower alkyl;

or of a N-oxide or a possible tautomer thereof;

or a pharmaceutically acceptable salt thereof.

5. A compound of Formula (I) according to claim 1, wherein

X is O or S;

Y is —NH—;

$Z_1$, $Z_2$, $Z_3$ and $Z_4$ are independently $CR_5$ or N;

A is direct bond;

B is direct bond;

$R_1$ is aryl or heterocyclyl;

Cy is cyclopropyl, cyclobutyl, cyclopentyl or cyclohexyl;

$R_2$ is selected from halogen-lower alkyl, lower alkyl, lower alkenyl, lower alkynyl, $C_0$–$C_6$cyano, $C_0$–$C_6$hydroxy, $C_0$–$C_6$alkoxy, $C_0$–$C_6$alkoxyalkoxyl, $C_0$–$C_6$amino, $C_0$–$C_6$alkoxyamino, $C_0$–$C_6$carboxy, $C_0$–$C_6$carboxyalkyl, $C_0$–$C_6$carbonylamino, $C_0$–$C_6$carbonylalkyl, $C_0$–$C_6$oxycarbonylalkyl, $C_0$–$C_6$oxycarbonylamino, $C_0$–$C_6$aminocarbonylalkyl, $C_0$–$C_6$aminocarbonyloxyalkyl, $C_0$–$C_6$aminocarbonylamino, $C_0$–$C_6$aminosulfonylalkyl, $C_0$–$C_6$cycloalkyl, $C_0$–$C_6$cycloalkenyl, $C_0$–$C_6$aryl, $C_0$–$C_6$oxyaryl, $C_0$–$C_6$alkoxyaryl, $C_0$–$C_6$aminoaryl, $C_0$–$C_6$aminoalkylaryl, $C_0$–$C_6$heterocyclyl, $C_0$–$C_6$oxyheterocyclyl, $C_0$–$C_6$alkoxyheterocyclyl, $C_0$–$C_6$aminoheterocyclyl and $C_0$–$C_6$aminoalkylheterocyclyl; wherein any above $C_1$–$C_6$ groups and amino groups can be optionally unsubstituted, mono-substituted or possibly disubstituted by lower alkyl;

$R_1$ and $R_2$ are combined together as a fined spiro ring G comprising C, N, O or S, wherein ring G is selected from cycloalkyl, cycloalkenyl, aryl and heterocyclyl, which can be saturated or partially saturated and unsubstituted, mono or polysubstituted;

V is C, N or $SO_2$;

W and W' are independently of each other hydrogen, halogen or lower alkyl; or together with the carbon atom to form a cycloalkyl, a cycloalkenyl, or a heterocyclyl ring;

n is an integer from 0 to 6;

$R_3$ is a heterocyclyl or an aryl;

$R_4$ is H or a lower alkyl;

$R_5$ is H, halogen or lower alkyl;

or of a N-oxide or a possible tautomer thereof;

or a pharmaceutically acceptable salt thereof.

6. A compound of Formula (I) according to claim 1, wherein

X is O;

Y is —NH—;

$Z_1$, $Z_2$, $Z_3$ are carbon and $Z_4$ is independently carbon or nitrogen;

A is direct bond;

B is direct bond;

$R_1$ is phenyl;

Cy is cyclopropyl, cyclobutyl, cyclopentyl or cyclohexyl;

R₂ is selected from:
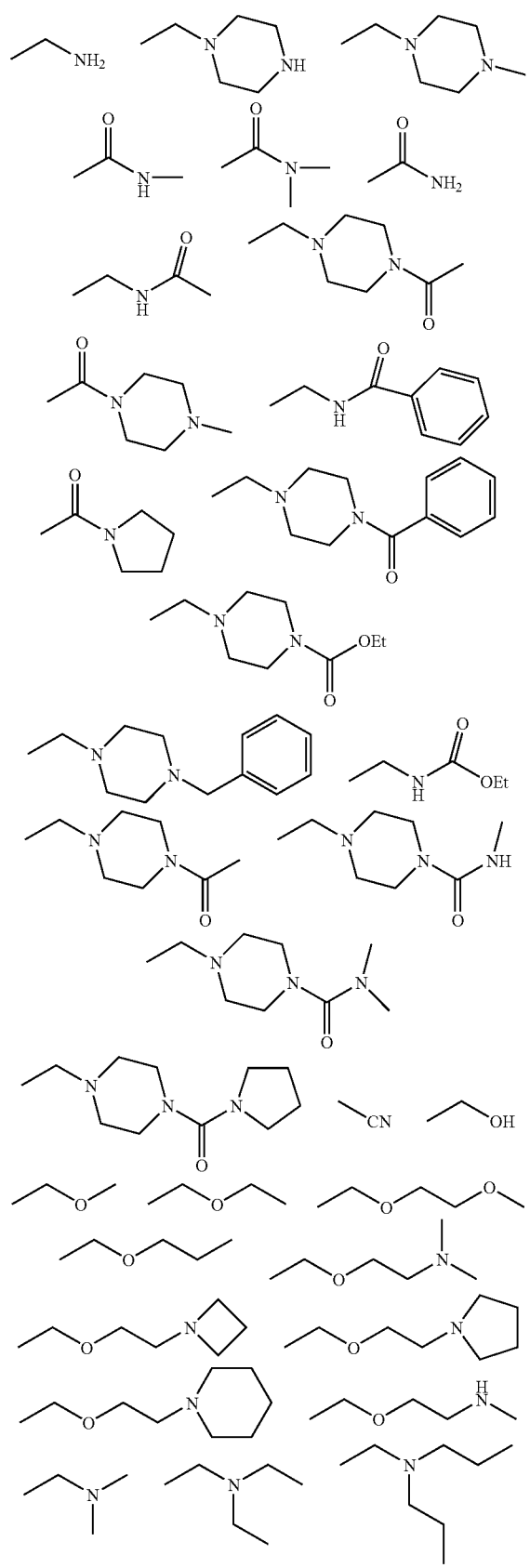
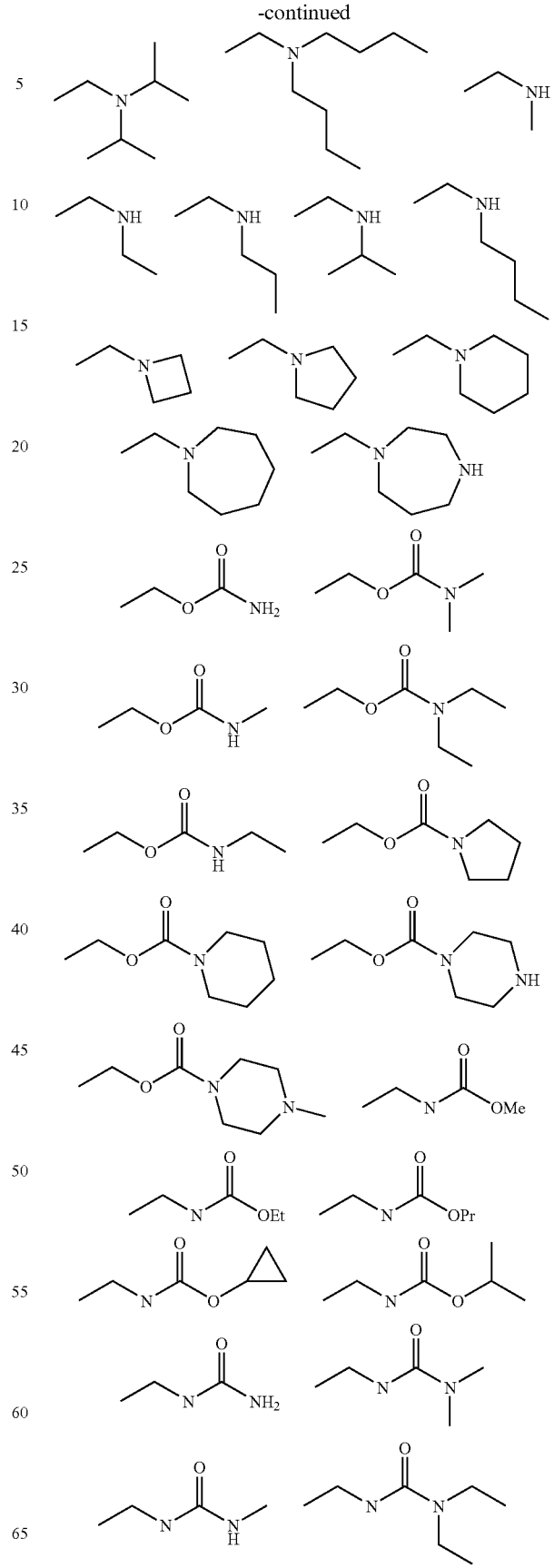

-continued

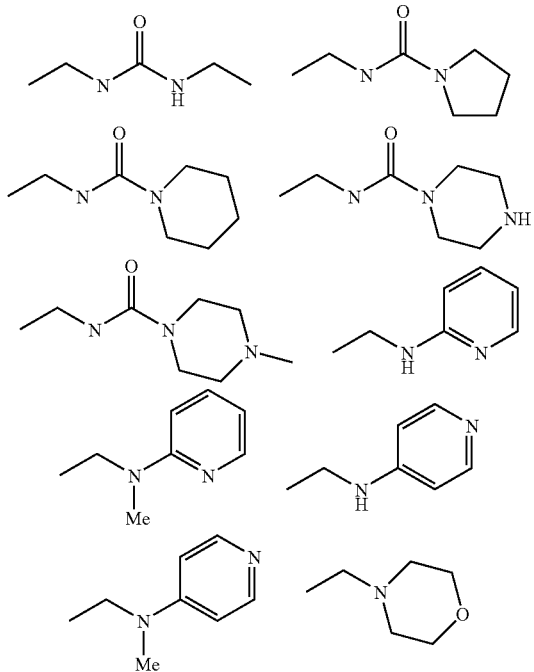

V is C, N or SO₂;
W and W' are independently of each other hydrogen;
n is an integer from 0 to 3;
R₃ is selected from:

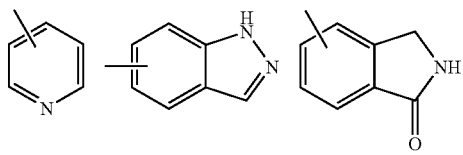

R₄ is H;
R₅ is H, F, Cl or CH₃;
or of a N-oxide or a possible tautomer thereof;
or a pharmaceutically acceptable salt thereof.

7. A compound of Formula (I) according to claim 1 selected from:
N-[4-(cyanocyclobutyl)-phenyl]{2-[(4-pyridylmethyl)amino]phenyl}carboxamide
N-[4-(cyanocyclopropyl)-phenyl]{2-[(4-pyridylmethyl)amino]phenyl}carboxamide
N-[4-(cyanocyclopentyl)-phenyl]{2-[(4-pyridylmethyl)amino]phenyl}carboxamide
N-[4-(cyanocyclohexyl)-phenyl]{2-[(4-pyridylmethyl)amino]phenyl}carboxamide
N-[4-(cyanocyclobutyl)phenyl]{2-[(4-pyridylmethyl)amino](3-pyridyl)}carboxamide
N-[4-(cyanocyclopropyl)-phenyl]{2-[(4-pyridylmethyl)amino](3-pyridyl)}carboxamide
N-[4-(cyanocyclopentyl)-phenyl]{2-[(4-pyridylmethyl)amino](3-pyridyl)}carboxamide
N-[4-(cyanocyclohexyl)-phenyl]{2-[(4-pyridylmethyl)amino](3-pyridyl)}carboxamide
N-{4-[(methoxymethyl)cyclobutyl]phenyl}{2-[(4-pyridylmethyl)amino]phenyl}carboxamide
N-{4-[(methoxymethyl)cyclobutyl]phenyl}{2-[(4-pyridylmethyl)amino](3-pyridyl)}carboxamide
N-{4-[(hydroxymethyl)cyclobutyl]phenyl}{2-[(4-pyridylmethyl)amino]phenyl}carboxamide
N-{4-[(hydroxymethyl)cyclobutyl]phenyl}{2-[(4-pyridylmethyl)amino](3-pyridyl)}carboxamide
N-{4-[(methoxymethyl)cyclopentyl]phenyl}{2-[(4-pyridylmethyl)amino](3-pyridyl)}carboxamide
N-{4-[(methoxymethyl)cyclohexyl]phenyl}{2-[(4-pyridylmethyl)amino](3-pyridyl)}carboxamide
N-(7-oxospiro[cyclopentane-1,3'-indoline]-11-yl){2-[(4-pyridylmethyl)amino]phenyl}carboxamide
N-(7-oxospiro[cyclopentane-1,3'-indoline]-11-yl){2-[(4-pyridylmethyl)amino]phenyl}carboxamide
N-(5-oxospiro[cyclopropane-1,3'-indoline]-9-yl){2-[(4-pyridylmethyl)amino]phenyl}carboxamide
N-(5-oxospiro[cyclopropane-1,3'-indoline]-9-yl){2-[(4-pyridylmethyl)amino](3-pyridyl)}carboxamide
N-[4-(cyanocyclopentyl)phenyl][2-(1H-indazol-6-ylamino)(3-pyridyl)]carboxamide
N-[4-(cyanocyclobutyl)phenyl][2-(1H-indazol-6-ylamino)(3-pyridyl)]carboxamide
N-[4-(cyanocyclopropyl)phenyl][2-(1H-indazol-6-ylamino)(3-pyridyl)]carboxamide
or of a N-oxide or a possible tautomer thereof;
or a pharmaceutically acceptable salt thereof.

8. A pharmaceutical composition which comprises as an active ingredient a compound as defined in any one of claims 1 to 7 or a pharmaceutically acceptable salt of the compound, or a hydrate or solvate of the compound and a pharmaceutically acceptable carrier.

* * * * *